(12) United States Patent
Guillon et al.

(10) Patent No.: US 7,893,309 B2
(45) Date of Patent: Feb. 22, 2011

(54) PROCESS FOR ISOMERIZING AN AROMATIC C8 CUT IN THE PRESENCE OF A CATALYST BASED ON A DEALUMINATED EUO ZEOLITE

(75) Inventors: Emmanuelle Guillon, Vernaison (FR); Eric Sanchez, Saint Genis Laval (FR)

(73) Assignee: IFP Energies Nouvelles, Rueil Malmaison Cedex (FR)

( * ) Notice: Subject to any disclaimer, the term of this patent is extended or adjusted under 35 U.S.C. 154(b) by 381 days.

(21) Appl. No.: 12/081,870

(22) Filed: Apr. 22, 2008

(65) Prior Publication Data

US 2008/0275281 A1 Nov. 6, 2008

(30) Foreign Application Priority Data

Apr. 23, 2007 (FR) .................. 07 02941

(51) Int. Cl.
*C07C 5/27* (2006.01)
(52) U.S. Cl. ...................... 585/481; 585/482
(58) Field of Classification Search ................ 585/481, 585/482
See application file for complete search history.

(56) References Cited

U.S. PATENT DOCUMENTS

| 4,695,667 | A | 9/1987 | Sumitani et al. |
| 6,057,486 | A | 5/2000 | Merlen et al. |
| 6,313,363 | B1 * | 11/2001 | Joly et al. ............... 585/480 |
| 2003/0127356 | A1 | 7/2003 | Benazzi et al. |

FOREIGN PATENT DOCUMENTS

| EP | 0 923 987 A | 6/1999 |
| FR | 2 765 209 A1 | 12/1998 |

OTHER PUBLICATIONS

Preliminary Report on Patentability completed Nov. 20, 2007 in French application No. 07/02.941.
Rao, G.N. et al., "Thermal and Hydrothermal Stabilities of Zeolite EU-1," Applied Catalysis A: General, vol. 119, 1994, pp. 33-43, XP002055790.

* cited by examiner

*Primary Examiner*—Thuan Dinh Dang
(74) *Attorney, Agent, or Firm*—Millen, White, Zelano & Branigan, P.C.

(57) ABSTRACT

A process is described for isomerising an aromatic cut containing at least one aromatic compound containing eight carbon atoms per molecule, comprising bringing said cut into contact with a catalyst containing a zeolite with structure type EUO, said catalyst having been prepared using a process comprising at least the following steps:
i) synthesizing at least one zeolite with structure type EUO having an overall Si/Al atomic ratio in the range 5 to 45;
ii) dealuminating the zeolite obtained at the end of said step i) using at least one treatment with an aqueous solution of a mineral acid or an organic acid, such that at least 10% by weight of the aluminium atoms are extracted from said zeolite from said step i);
iii) forming said dealuminated zeolite with a matrix;
iv) depositing at least one metal from group VIII of the periodic table of the elements, the order of carrying out said steps iii) and iv) being inconsequential following on from said step ii).

16 Claims, No Drawings

PROCESS FOR ISOMERIZING AN AROMATIC C8 CUT IN THE PRESENCE OF A CATALYST BASED ON A DEALUMINATED EUO ZEOLITE

FIELD OF THE INVENTION

The present invention relates to the isomerization of an aromatic cut containing at least one aromatic compound containing eight carbon atoms per molecule with a view to the production of xylenes. Said aromatic cut envisaged for the present invention is a feed containing a mixture of xylenes, ethylbenzene alone or a mixture of xylenes and ethylbenzene. This feed is usually termed an "aromatic C8 cut".

More particularly, the present invention relates to a process for isomerizing an aromatic feed comprising at least one aromatic compound containing eight carbon atoms per molecule which is aimed at maximizing the production of para-xylene.

PRIOR ART

Catalysis of the isomerization of ethylbenzene into xylenes necessitates the presence of a group VIII metal. Optimized formulations based on mordenite and a group VIII metal produce catalysts on which side reactions are still non-negligible. An example which may be cited is the opening of naphthene rings, which may or may not be followed by cracking or disproportionation and transalkylation of C8 aromatics, which results in the formation of unwanted aromatic compounds. Thus, it is of particular interest to discover novel, more selective catalysts.

Zeolites used for isomerizing a C8 aromatic cut include ZSM-5, used alone or mixed with other zeolites such as mordenite, for example. Said catalysts have been described in U.S. Pat. No. 4,467,129, U.S. Pat. No. 4,482,773 and EP-B 0 013 617. Other catalysts principally based on mordenite have been described, for example, in U.S. Pat. No. 4,723,051, U.S. Pat. No. 4,665,258 and in French patent application FR-A-2 477 903. More recently, a catalyst based on a zeolite with structure type EUO (EP-A1-0 923 987) has been proposed. International patent application WO-A-2005/065380 describes the use of a zeolite with structure type MTW for the isomerization of xylenes and ethylbenzene.

SUMMARY AND ADVANTAGE OF THE INVENTION

The present invention concerns a process for isomerising an aromatic cut containing at least one aromatic compound containing eight carbon atoms per molecule, comprising bringing said cut into contact with at least one catalyst containing at least one zeolite with structure type EUO, said catalyst having been prepared using a process comprising at least the following steps:

i) synthesizing at least one zeolite with structure type EUO having an overall Si/Al atomic ratio in the range 5 to 45;

ii) dealuminating the zeolite obtained at the end of said step i) using at least one treatment with an aqueous solution of a mineral acid or an organic acid, such that at least 10% by weight of the aluminium atoms are extracted from said zeolite resulting from said step i);

iii) forming said dealuminated zeolite with a matrix;

iv) depositing at least one metal from group VIII of the periodic table of the elements, the order of carrying out said steps iii) and iv) being inconsequential following on from said step ii).

It has surprisingly been discovered that a catalyst in the form of extrudates or beads comprising at least one zeolite with structure type EUO which has been dealuminated so that at least 10% by weight of the aluminium atoms of the zeolite with structure type EUO in its as-synthesized form has been extracted, at least one matrix and at least one metal from group VIII of the periodic table of the elements results in improved catalytic performances as regards selectivity when it is used in a process for isomerization of an aromatic cut comprising at least one aromatic compound containing eight carbon atoms per molecule. In particular, such a catalyst is more selective towards the desired products, namely xylenes and in particular para-xylene, than a prior art catalyst based on a zeolite with a non-dealuminated EUO type structure. This enhanced selectivity towards the isomerization of xylenes is to the detriment of the unwanted side reactions of cracking, dealkylation, transalkylation and disproportionation. Dealumination of the zeolite obtained at the end of said step i) of the process of the invention is carried out by means of at least one treatment with an aqueous solution of a mineral acid or an organic acid.

DESCRIPTION OF THE INVENTION

The present invention provides a process for isomerising an aromatic cut containing at least one aromatic compound containing eight carbon atoms per molecule, comprising bringing said cut into contact with at least one catalyst containing at least one zeolite with structure type EUO, said catalyst having been prepared using a process comprising at least the following steps:

i) synthesizing at least one zeolite with structure type EUO having an overall Si/Al atomic ratio in the range 5 to 45;

ii) dealuminating the zeolite obtained at the end of said step i) using at least one treatment with an aqueous solution of a mineral acid or an organic acid, such that at least 10% by weight of the aluminium atoms are extracted from said zeolite resulting from said step i);

iii) forming said dealuminated zeolite with a matrix;

iv) depositing at least one metal from group VIII of the periodic table of the elements, the order of carrying out said steps iii) and iv) being inconsequential following on from said step ii).

The zeolite with structure type EUO, dealuminated by at least one treatment with an aqueous solution of a mineral acid or an organic acid present in the catalyst used to carry out the isomerization process of the invention, is a zeolite selected from EU-1 zeolite, TPZ-3 zeolite and ZSM-50 zeolite; preferably it is an EU-1 zeolite. EU-1, TPZ-3 and ZSM-50 zeolites with structure type EUO are well known in the art ("Atlas of zeolite framework types", Ch Baerlocher, W M Meier and D H Olson, 5$^{th}$ edition, 2001). It is known that a zeolite with structure type EUO, in particular an EU-1 zeolite, has a one-dimensional microporous network with a pore diameter of 4.1×5.4 Å (1 Å=1 Angstrom=$10^{-10}$ m). Further, N A Briscoe et al have disclosed, in an article in the review Zeolites (1988, 8, 74), that these one-dimensional channels have side pockets with a depth of 8.1 Å and a diameter of 6.8×5.8 Å.

The mode of preparation of the various zeolites with structure type EUO is also well known to the skilled person. In general, the methods for preparing such zeolites comprise mixing a source of silicon, a source of aluminium, a source of an alkali metal and a nitrogen-containing organic compound acting as a template in an aqueous medium. The EU-1 zeolite described in European patent application EP-A-0 042 226 is prepared using either the alkylated derivative of an α-ω polymethylene diammonium compound as a template or a degradation product of that derivative, or even precursors of that derivative. TPZ-3 zeolite described in European patent application EP-A-0 051 318 is prepared using the same family of template as that employed to synthesize EU-1 zeolite. In particular, it describes the use of the compound 1,6-N,N,N,N',N',N',-hexamethylhexamethylene diammonium. ZSM-50 zeolite described in documents EPO 159 845 and U.S. Pat. No. 4,640,829 is prepared using the dibenzyldimethylammonium derivative (DBDMA) as the template. In addition, to carry out said step i) for preparing the zeolite with structure type EUO present in the catalyst used in the isomerization process of the invention, the skilled person will be able to make use of one or other of the references cited above describing the preparation of such zeolites.

More precisely, to prepare an EU-1 zeolite according to said step i), the following are mixed in an aqueous medium: at least one source of silicon, at least one source of aluminium, at least one nitrogen-containing organic template Q with formula $R_1R_2R_3$—$N^+$—$(CH_2)_n$—$N^+$—$R_4R_5R_6$ in which n is in the range 3 to 12, groups $R_1$ to $R_6$, which may be identical or different, are alkyl groups containing 1 to 8 carbon atoms, up to five of said groups $R_1$ to $R_6$ possibly being hydrogen, and optionally zeolitic seeds.

The reaction mixture has the following molar composition:
$SiO_2/Al_2O_3$: 10-150;
$OH^-/SiO_2$: 0.1-6;
$(M^++Q)/Al_2O_3$: 0.5-100;
$Q/(M^++Q)$: 0.1-10;
$H_2O/SiO_2$: 1-100.

Q is the cation $R_1R_2R_3$—$N^+$—$(CH_2)_n$—$N^+$—$R_4R_5R_6$ described above, preferably 1,6-N,N,N,N',N',N',-hexamethylhexamethylene diammonium, and $M^+$ is an alkali or ammonium cation.

Said reaction mixture is reacted under autogenous pressure, optionally with addition of a gas, for example nitrogen, at a temperature in the range 85° C. to 250° C. until crystals of the EU-1 zeolite are formed. The reaction period is in the range from 1 minute to a few months depending on the composition of the reagents, the mode of heating and mixing, the reaction temperature and the stirring mode. At the end of the reaction, the solid phase is collected on a filter and washed. At this stage, the EU-1 zeolite is termed "as-synthesized" and contains in its intra-crystalline pores at least the cation $R_1R_2R_3$—$N^+$—$(CH_2)_n$—$N^+$—$R_4R_5R_6$, preferably 1,6-N,N,N,N',N',N',-hexamethylhexamethylene diammonium. In accordance with the invention, said as-synthesized EU-1 zeolite obtained at the end of step i) has an overall Si/Al atomic ratio in the range 5 to 45, preferably in the range 10 to 40 and more preferably in the range 10 to 25. The overall Si/Al atomic ratio, determined by X ray fluorescence or atomic absorption, takes into account both the aluminium atoms present in the zeolitic framework and any aluminium atoms which may be present outside said zeolitic framework, also termed extra-lattice aluminium.

Step ii) of the process for preparing a zeolite with structure type EUO, preferably EU-1 zeolite, present in the catalyst used to carry out the isomerization process of the invention, consists of extracting at least 10% by weight, preferably at least 20% by weight, of the aluminium atoms from said zeolite with structure type EUO, preferably EU-1 zeolite, resulting from said step i) in its as-synthesized form. As a result, the dealuminated zeolite with structure type EUO, preferably dealuminated EU-1 zeolite, obtained at the end of said step ii) has an overall Si/Al atomic ratio which is higher than that of the as-synthesized zeolite with structure type EUO, preferably as-synthesized EU-1 zeolite, which has not yet been dealuminated. Step ii) of the process for the preparation of the catalyst is carried out by subjecting the zeolite obtained at the end of said step i) to at least one treatment with an aqueous solution of a mineral acid or an organic acid.

In accordance with a first implementation of said dealumination step ii), the zeolite with structure type EUO, preferably EU-1 zeolite, resulting from said step i), undergoes calcining in a stream of dry air at a temperature in the range 400° C. to 600° C., then undergoes at least one treatment with an aqueous solution of a mineral acid or an organic acid. The duration of the calcining step can vary and is in the range from a few hours to a few days. The calcining treatment carried out on said zeolite with structure type EUO resulting from said step i) is intended to eliminate the organic template present in the micropores of the zeolite, for example the cation $R_1R_2R_3$—$N^+$—$(CH_2)_n$—$N^+$—$R_4R_5R_6$, preferably 1,6-N,N,N,N',N',N',-hexamethylhexamethylene diammonium, when the zeolite synthesized during said step i) is EU-1 zeolite. The percentage by weight of residual carbon in the zeolite resulting from said calcining step is preferably less than 0.3% and still more preferably less than 0.1%.

Said treatment of the zeolite with structure type EUO, preferably EU-1 zeolite, with an aqueous solution of a mineral or organic acid carried out after the calcining step is also termed the "acid attack step". Said treatment may be repeated as many times as is necessary to obtain the desired degree of dealumination. In this case, the zeolite is washed with distilled water between each successive acid attack step.

Preferably, one or more ion exchange step(s) using at least one $NH_4NO_3$ solution is (are) carried out between calcining in a stream of dry air and treatment with an aqueous acidic solution to eliminate at least part, preferably practically all of the alkali cation, in particular sodium, which may be present in the cationic position in the as-synthesized form of the zeolite. Each exchange step is carried out at a temperature which is preferably in the range 50° C. to 150° C. for a period which is advantageously in the range from 2 hours to 10 hours. In general, an aqueous solution of ammonium nitrate $NH_4NO_3$ with a normality in the range 7N to 12N is used. Similarly, at the end of said dealumination step ii) when treatment(s) is (are) carried out with an aqueous acid solution, it is possible to carry out one or more ion exchange step(s) using at least one $NH_4NO_3$ solution, to eliminate residual alkali cations and in particular sodium.

In order for the zeolite resulting from said step ii) to have the desired overall Si/Al atomic ratio after extracting at least 10% by weight of the aluminium atoms from the zeolite with structure type EUO resulting from said step i), it is necessary to select and control the operating conditions of each acid attack step carefully. In particular, the temperature at which the treatment with the aqueous solution of mineral or organic acid is carried out, the nature and concentration of the acid used, the ratio between the quantity of acid solution and the weight of zeolite treated, the duration of the treatment and the number of treatments carried out are significant parameters when carrying out each acid attack step. Advantageously, the treatment of the zeolite with an aqueous solution of a mineral acid or an organic acid is carried out at a temperature in the range 30° C. to 120° C., preferably in the range 50° C. to 120° C., more preferably in the range 60° C. to 100° C. The concentration of acid in the aqueous solution is generally in the range 0.05 to 20 mol/l, preferably in the range 0.1 to 10 mol/l, and more preferably in the range 0.5 to 5 mol/l. The ratio between the volume V of the acid solution in ml and the weight P of treated zeolite, in g, is generally in the range 1 to 50, preferably in the range 2 to 20. The duration of the acid attack is generally more than 1 hour, usually in the range 2 hours to 10 hours, and preferably in the range 2 hours to 8 hours. The acid selected to carry out said acid attack step is either a mineral acid or an organic acid, preferably a mineral acid selected from nitric acid $HNO_3$, hydrochloric acid HCl and sulphuric acid $H_2SO_4$. Highly preferably, it is nitric acid. When an organic acid is used for acid attack, acetic acid $CH_3COOH$ is preferred. The number of successive treatments of the zeolite with an aqueous acid solution is preferably less than 4. In the case in which several acid attacks are carried out in succession, various concentrations of the aqueous solutions of mineral acid or organic acid may be used.

After carrying out the treatment(s) with an aqueous acid solution, the zeolite is then washed with distilled water and dried at a temperature in the range 80° C. to 140° C. for a period in the range 10 to 48 hours.

This dealumination method carried out in accordance with said first mode for the implementation of step ii) of the process for preparing a zeolite with structure type EUO present in the catalyst used to carry out the isomerization process of the invention is termed the direct acid attack method.

In accordance with a second implementation of said dealumination step ii), the zeolite with structure type EUO, preferably EU-1 zeolite, resulting from said step i), undergoes calcining in a stream of dry air at a temperature in the range 400° C. to 600° C. then one or more ion exchange(s) with at least one $NH_4NO_3$ solution and then undergoes at least one cycle for dealumination of the zeolitic framework comprising at least one heat treatment carried out in the presence of steam and at least one acid attack using at least one aqueous solution of a mineral or organic acid.

The duration of calcining in dry air can vary and is in the range from a few hours to a few days. The calcining treatment of the zeolite with structure type EUO resulting from said step i) is intended to eliminate the organic template present in the micropores of said zeolite, for example the cation $R_1R_2R_3$—$N^+$—$(CH_2)_n$—$N^+$—$R_4R_5R_6$, preferably 1,6-N,N,N,N',N',N',-hexamethylhexamethylene diammonium when the zeolite synthesized during said step i) is EU-1 zeolite. Ion exchange(s) subsequent to said calcining in a stream of dry air can eliminate at least part, preferably almost all, of the alkali cation, in particular sodium which may be present in the cationic position in the zeolite in its as-synthesized from. Each exchange is carried out at a temperature which is preferably in the range 50° C. to 150° C. for a period which is advantageously in the range 2 hours to 10 hours. In general, an aqueous solution of ammonium nitrate $NH_4NO_3$ with a normality in the range 7N to 12N is used.

The operating conditions for heat treatment in the presence of steam, in particular the temperature and duration of said treatment and the percentage by volume of the steam, as well as the operating conditions for the post-heat treatment acid attack, in particular the duration of the acid attack, the nature and the concentration of the acid used, and the ratio between the volume of the acid solution and the weight of the zeolite treated, are adapted so as to obtain a zeolite with a dealuminated structure type EUO, preferably a dealuminated EU-1 zeolite, with the desired overall Si/Al atomic ratio after extracting at least 10% by weight of the aluminium atoms present in the as-synthesized zeolite resulting from said step i). Advantageously, the heat treatment in the presence of steam is carried out at a temperature in the range 200° C. to 900° C., preferably in the range 300° C. to 900° C., more preferably in the range 400° C. to 600° C. The duration of said heat treatment is generally 0.5 hours or more, preferably in the range 0.5 hours to 24 hours, and highly preferably in the range 0.5 hours to 12 hours. The percentage by volume of steam during the heat treatment is generally in the range 5% to 100%, preferably in the range 20% to 100%, and more preferably in the range 40% to 100%. The volume fraction other than steam which may optionally be present is constituted by air. The flow rate of the gas formed by steam and optionally by air is in the range 0.2 l/h/g of treated solid to 10 l/h/g of treated solid.

The temperature at which the acid attack is carried out, subsequent to the heat treatment in the presence of steam, is generally in the range 30° C. to 120° C., preferably in the range 50° C. to 120° C., more preferably in the range 60° C. to 100° C. The concentration of acid in the aqueous solution is generally in the range 0.05 to 20 mol/l, preferably in the range 0.1 to 10 mol/l, more preferably in the range 0.5 to 5 mol/l. The ratio between the volume V of the aqueous acid in ml and the weight P of the treated zeolite in grams is generally in the range 1 to 50, preferably in the range 2 to 20. The duration of the acid attack is generally more than 1 hour, usually in the range 2 hours to 10 hours, preferably in the range 2 hours to 8 hours. The acid selected to carry out the acid attack is either a mineral acid or an organic acid; it is preferably a mineral acid selected from nitric acid $HNO_3$, hydrochloric acid HCl and sulphuric acid $H_2SO_4$. Highly preferably, it is nitric acid. When an organic acid is used for the acid attack, acetic acid $CH_3COOH$ is preferred.

The cycle for dealumination of the zeolitic framework comprising at least one heat treatment carried out in the presence of steam and at least one acid attack using at least one aqueous solution of a mineral or organic acid may be repeated as many times as is necessary to obtain the dealuminated zeolite with structure type EUO, preferably dealuminated EU-1 zeolite, having the desired characteristics, in particular an overall Si/Al atomic ratio which is higher than that of the zeolite in its as-synthesized form after extraction of at least 10% by weight, preferably at least 20% by weight of the aluminium atoms from the as-synthesized zeolite. The number of dealumination cycles is preferably less than 4.

This dealumination method carried out in accordance with said second mode for implementation of step ii) of the process for preparing a zeolite with structure type EUO present in the catalyst used to carry out the isomerization process of the invention is termed the heat treatment and acid attack method.

In accordance with a third implementation of said dealumination step ii), the zeolite with structure type EUO, preferably EU-1 zeolite, resulting from said step i) undergoes a heat treatment carried out in the presence of steam at a temperature in the range 450° C. to 850° C., then at least one treatment with an aqueous solution of a mineral or organic acid. Said treatment(s) with an aqueous solution of acid is (are) preferably followed by one or more ion exchange(s) using at least one $NH_4NO_3$ solution to eliminate practically all of the alkali cations, in particular sodium, which may be present in the cationic position in the zeolite in its as-synthesized form. Each exchange is carried out at a temperature which is preferably in the range 50° C. to 150° C. for a period which is advantageously in the range 2 hours to 10 hours. In general, an aqueous solution of ammonium nitrate $NH_4NO_3$ with a normality in the range 7N to 12N is used.

In accordance with said third implementation of said step ii), said heat treatment in the presence of steam is carried out simultaneously with the elimination of the organic template, preferably the cation $R_1R_2R_3$—$N^+$—$(CH_2)_n$—$N^+$—$R_4R_5R_6$ and highly preferably 1,6-N,N,N,N',N',N',-hexamethylhexamethylene diammonium, present in the micropores of said zeolite. The heat treatment in the presence of steam is carried out at a temperature which is sufficiently high to allow elimination of said template. The operating conditions for carrying out said heat treatment in the presence of steam are identical to those given above for carrying out heat treatment in the presence of steam carried out in the dealumination cycle of the second implementation of dealumination step ii). The treatment with an aqueous solution of a mineral or organic acid is carried out under the same operating conditions as those given above for carrying out acid attack by at least one aqueous solution of a mineral or organic acid used in the dealumination cycle of the second implementation of dealumination step ii). Following the heat treatment carried out in the presence of steam, several successive acid attacks may be carried out to obtain the desired degree of dealumination. The aqueous acid solutions used to carry out these various acid attack steps have an identical or different concentration, preferably different. Between each acid attack step, the zeolite is washed with distilled water.

At the end of said dealumination step ii), carried out by subjecting the zeolite obtained at the end of said step i) to at least one treatment with an aqueous solution of a mineral acid or an organic acid in accordance with the first, the second or the third implementation described above, at least 10% by weight of the aluminium atoms, preferably at least 20% by weight of the aluminium atoms present in the as-synthesized zeolite with structure type EUO, preferably as-synthesized EU-1 zeolite, have been extracted. The dealuminated zeolite with structure type EUO, preferably dealuminated EU-1 zeolite, obtained at the end of said step ii) has a crystallinity of more than 85%, preferably more than 90%, and more preferably more than 97%. The crystallinity is calculated from a diffraction diagram by comparison with a reference zeolite with structure type EUO. The crystallinity corresponds to the ratio of the surface area of peaks in the solids analyzed to the surface area of peaks in the reference zeolite with structure type EUO in the diffraction angle range of $2\theta=8°$ to $40°$. The dealuminated zeolite with structure type EUO, preferably dealuminated EU-1 zeolite, obtained at the end of step ii) is free of mesopores: no mesoporous cavities with a size in the range 2 to 50 nm are created following implementation of dealumination step ii).

After carrying out dealumination step ii), the dealuminated zeolite with structure type EUO, preferably dealuminated EU-1 zeolite, is then washed with water and dried at a temperature in the range 80° C. to 140° C. for a period in the range 10 to 48 hours.

For the purposes of its use in the isomerization process of the invention, the preparation of the catalyst comprising a dealuminated zeolite with structure type EUO, preferably dealuminated EU-1 zeolite, is continued by carrying out said step iii) for forming and by carrying out said step iv) for depositing at least one metal from group VIII of the periodic table of the elements. The order of carrying out said steps iii) and iv), subsequent to said step ii), is of no consequence. Preferably, said step iii) precedes said step iv).

In order to carry out said step iii) for forming said dealuminated zeolite with structure type EUO, preferably dealuminated EU-1 zeolite, a matrix is used selected from clays, magnesia, aluminas, silicas, titanium oxide, boron oxide, zirconia, aluminium phosphates, titanium phosphates, zirconium phosphates, silica-aluminas and coal or a mixture of at least two of said compositions. Preferably, the matrix is an alumina. Advantageously, the zeolite associated with the matrix is formed into beads or extrudates, highly advantageously into the form of extrudates.

More particularly, forming in accordance with said step iii) consists of mixing the dealuminated EUO zeolite, preferably dealuminated EU-1 zeolite, into a moist matrix gel, preferably alumina, generally obtained by mixing at least one acid and a matrix powder for the period necessary to obtain good homogeneity of the paste, i.e. for about ten minutes, for example, then passing the paste obtained through a die to form extrudates, for example with a diameter of 0.4 to 4 mm. Forming is generally followed by drying then calcining. Drying is advantageously carried out at a temperature in the range 100° C. to 150° C. for a period in the range 5 to 20 hours in an oven. Calcining is advantageously carried out at a temperature in the range 250° C. to 600° C. for a period in the range 1 to 8 hours.

Step iv) for preparing the catalyst comprising a dealuminated EUO zeolite, preferably a dealuminated EU-1 zeolite, consists of introducing at least one metal from group VIII of the periodic table of the elements and optionally at least one metal selected from metals from groups IIIA, IVA and VIIB.

Said group VIII metal present in the catalyst used in the isomerization process of the invention is selected from iron, cobalt, nickel, ruthenium, rhodium, palladium, osmium, iridium and platinum, preferably from the noble metals and highly preferably from palladium and platinum. More preferably, said group VIII metal is platinum. In accordance with the method for depositing said group VIII metal, as indicated below in the description, said group VIII metal, preferably platinum, may be deposited primarily on the dealuminated zeolite or on the matrix.

Said metal selected from metals from groups IIIA, IVA and VIIB which are optionally present in the catalyst of the invention is selected from gallium, indium, tin and rhenium, preferably from indium, tin and rhenium.

The catalyst used in the isomerization process of the invention may be prepared using any method which is known to the skilled person. Preferably, following calcining carried out at the end of forming step iii), at least one group VIII metal is introduced onto the zeolitic support, namely either mainly onto the matrix or mainly onto the dealuminated zeolite or onto the modified zeolite-matrix ensemble. Said metal is advantageously deposited on the zeolitic support using the dry impregnation technique, the excess impregnation technique or by ion exchange. When a plurality of metals are introduced, these may be introduced either all in the same manner or using different techniques.

Any group VIII metal precursor is suitable for depositing one or more of the group VIII metal(s) on the zeolitic support. In particular, for any noble metal from group VIII, it is possible to use ammonia compounds or compounds such as ammonium chloroplatinate, dicarbonyl platinum dichloride, hexahydroxyplatinic acid, palladium chloride or palladium nitrate. The platinum is generally introduced in the form of hexachloroplatinic acid. The group VIII noble metal is preferably introduced by impregnation using an aqueous or organic solution of one of the metallic compounds cited above. Examples of suitable organic solvents which may be cited are paraffinic, naphthenic or aromatic hydrocarbons containing, for example, 6 to 12 carbon atoms per molecule, and halogenated organic compounds containing 1 to 12 carbon atoms per molecule, for example. Examples which may be cited are n-heptane, methylcyclohexane, toluene and chloroform. Mixtures of solvents may also be used.

Certain parameters employed during deposition, in particular the nature of the precursor of the group VIII metal(s) used, can be controlled to orientate the deposition of said metal(s) mainly on the matrix or on the zeolite.

Thus, to introduce the group VIII metal(s), preferably platinum and/or palladium, mainly onto the matrix, it is possible to carry out an anion exchange with hexachloroplatinic acid and/or hexachloropalladic acid in the presence of a competing agent, for example hydrochloric acid, deposition generally being followed by calcining, for example at a temperature in the range 350° C. to 550° C. for a period in the range 1 to 4 hours. With such precursors, the group VIII metal(s) is (are) deposited mainly on the matrix and said metal(s) are well dispersed and have good macroscopic distribution through the catalyst grain.

It is also possible to envisage depositing the group VIII metal(s), preferably platinum and/or palladium, by cation exchange so that said metal(s) are mainly deposited on the zeolite. Thus, in the case of platinum, the precursor may, for example, be selected from:

ammoniacal compounds such as platinum (II) tetrammine salts with formula $Pt(NH_3)_4X_2$, platinum (IV) hexammine salts with formula $Pt(NH_3)_6 \times 4$; platinum (IV) halogenopentammine salts with formula $(PtX(NH_3)_5)X_3$, platinum N-tetrahalogenodiammine salts with formula $PtX_4(NH_3)_2$; and halogenated compounds with formula $H(Pt(acac)_2X)$;

X being a halogen selected from the group formed by chlorine, fluorine, bromine and iodine, X preferably being chlorine, and "acac" representing the acetylacetonate group (with empirical formula $C_5H_7O_2$), derived from acetylacetone. With such precursors, the group VIII metal(s) is (are) mainly deposited on the zeolite and said metal(s) are well dispersed with good macroscopic distribution through the catalyst grain.

Dry impregnation of the group VIII metal onto the zeolitic support results in said metal being deposited both on the matrix and on the dealuminated zeolite.

In the case in which the catalyst used in the isomerization process of the invention also contains at least one metal selected from metals from groups IIIA, IVA and VIIB, any technique for depositing such a metal which is known to the skilled person and any precursor for such metals is suitable.

The group VIII metal(s) and that (those) from groups IIIA, IVA and VIIB may be added either separately or simultaneously in at least one unitary step. When at least one metal from groups IIIA, IVA and VIIB is added separately, it is preferable that it should be added after the group VIII metal.

The additional metal selected from metals from groups IIIA, IVA and VIIB may be introduced via compounds such as chlorides, bromides or nitrates of metals from groups IIIA, IVA and VIIB, for example. As an example, in the case of indium, the nitrate or chloride is advantageously used and in the case of rhenium, perrhenic acid is advantageously used. In the case of tin, the tin chlorides $SnCl_2$ and $SnCl_4$ are preferred. The additional metal selected from metals from groups IIIA, IVA and VIIB may also be introduced in the form of at least one organic compound selected from the group constituted by complexes of said metal, in particular polyketone complexes of the metal and hydrocarbyl metals such as metal alkyls, cycloalkyls, aryls, alkylaryls or arylalkyls. In this latter case, the metal is advantageously introduced using a solution of an organometallic compound of said metal in an organic solvent. It is also possible to use organohalogenated compounds of the metal. Particular examples of organic compounds of metals which may be cited are tetrabutyltin in the case of tin, and triphenylindium in the case of indium.

If the additional metal selected from metals from groups IIIA, IVA and VIIB is introduced before the group VIII metal, the compound of metal IIIA, IVA and/or VIIB employed is generally selected from the group constituted by the metal halide, nitrate, acetate, tartrate, carbonate and oxalate. Introduction is thus advantageously carried out in aqueous solution. However, it may also be introduced using a solution of an organometallic compound of a metal, for example tetrabutyltin. In this case, before introducing at least one metal from group VIII, calcining in air is carried out.

Further, intermediate treatments such as calcining and/or reduction may be carried out between successive deposits of the various metals.

The preparation of the catalyst is generally terminated by calcining, normally at a temperature in the range 250° C. to 600° C., for a period in the range 0.5 to 10 hours, preferably preceded by drying, for example oven drying, at a temperature from ambient temperature to 250° C., preferably 40° C. to 200° C. Said drying step is preferably carried out during the temperature ramp-up step necessary for carrying out said calcining. Prior reduction of the catalyst may be carried out ex situ in a stream of hydrogen, for example at a temperature of 450° C. to 600° C., for a period of 0.5 to 4 hours.

Said group VIII metal(s) is (are) advantageously deposited so that the dispersion of said metal(s), determined by chemisorption, is 50% to 100%, preferably 60% to 100% and more preferably 70% to 100%. Advantageously, said group VIII metal(s) is (are) deposited to obtain good distribution of said metal(s) in the formed catalyst. This distribution is characterized by its profile obtained using a Castaing microprobe. The ratio of the concentrations of each group VIII element in the core of the grain with respect to the edge of that grain, defined as the distribution coefficient, is advantageously from 0.7:1 to 1.3:1, preferably 0.8:1 to 1.2:1.

In the composition of the catalyst used in the isomerization process of the invention, the dealuminated zeolite with structure type EUO, preferably dealuminated EU-1 zeolite, is more particularly present in an amount of 1% to 90%, preferably 3% to 80% and more preferably 4% to 60% by weight with respect to the weight of catalyst. The group VIII metal (s), preferably platinum, deposited on the zeolite and/or on the matrix represent 0.01% to 4%, preferably 0.05% to 2.0% by weight with respect to the weight of catalyst. The matrix constitutes the complement to 100%. When said catalyst contains at least one metal selected from metals from groups IIIA, IVA and VIIB, the amount thereof may be up to 2% by weight with respect to the weight of catalyst. Advantageously, it is 0.01% to 2%, preferably 0.05% to 1.0% by weight.

When said catalyst contains sulphur, the amount thereof may be such that the ratio of the number of sulphur atoms to the number of group VIII metal atoms deposited is up to 2:1. It is advantageously 0.5:1 to 2:1.

The dealuminated zeolite with structure type EUO, preferably dealuminated EU-1 zeolite, present in the catalyst used to carry out the isomerization process of the invention is highly preferably in its protonated form (hydrogen form $H^+$) in which the proportion of cations other than $H^+$ is less than 30% of the total number of cations, preferably less than 20%; more preferably less than 10% and still more preferably less than 5% with respect to the total number of cations on the zeolite. This protonated form is generally obtained during heat treatment in the presence of steam employed when implementing said second and third implementations of said step ii) or during the calcining step subsequent to forming the dealuminated zeolite with a matrix.

In the case in which the catalyst does not contain any sulphur, reduction of the metal in hydrogen is carried out in situ before injecting the feed.

In the case in which the catalyst of the invention contains sulphur, the sulphur is introduced onto the catalyst which has been formed and calcined, containing the metal or metals cited above, either in situ before the catalytic reaction, or ex situ. Any sulphurization is carried out after reduction. In the case of in situ sulphurization, if the catalyst has not already been reduced, reduction is carried out before sulphurization.

In the case of ex situ sulphurization, reduction is carried out followed by sulphurization. Sulphurization is carried out in the presence of hydrogen using any sulphurizing agent which is well known to the skilled person, such as dimethyldisulphide or hydrogen sulphide. As an example, the catalyst is treated with a feed containing dimethyldisulphide in the presence of hydrogen, in a concentration so that the sulphur/metal atomic ratio is 1.5. The catalyst is then maintained for about 3 hours at about 400° C. in a stream of hydrogen before injecting the feed.

The isomerization process of the invention consists of bringing an aromatic cut containing at least one aromatic compound containing eight carbon atoms per molecule into contact with at least said catalyst containing at least said dealuminated zeolite with structure type EUO, preferably said dealuminated EU-1 zeolite, said catalyst having been prepared in accordance with each of said steps i), ii), iii) and iv) described above in the present description.

In particular, said aromatic cut containing at least one aromatic compound containing eight carbon atoms per molecule comprises either solely a mixture of xylenes or solely ethylbenzene, or a mixture of xylene(s) and ethylbenzene as the aromatic compound containing eight carbon atoms. Said isomerization process of the invention is generally carried out under the following operating conditions:

- a temperature in the range 300° C. to 500° C., preferably in the range 320° C. to 450° C. and more preferably in the range 340° C. to 430° C.;
- a partial pressure of hydrogen in the range 0.3 to 1.5 MPa, preferably in the range 0.4 to 1.2 MPa and more preferably in the range 0.7 to 1.2 MPa;
- a total pressure in the range 0.45 to 1.9 MPa, preferably in the range 0.6 to 1.5 MPa; and
- a space velocity, expressed in kilograms of feed introduced per kilogram of catalyst per hour, in the range 0.25 to 30 $h^{-1}$, preferably in the range 1 to 10 $h^{-1}$ and more preferably in the range 2 to 6 $h^{-1}$.

The following examples illustrate the invention without in any way limiting its scope.

Example 1

Preparation of a Dealuminated EU-1 Zeolite

The starting material used was an as-synthesized EU-1 zeolite comprising the organic template, namely 1,6-N,N,N,N',N',N',-hexamethylhexamethylene diammonium, which had an overall Si/Al atomic ratio of 15.3, and a sodium weight content corresponding to a Na/Al atomic ratio (as a %) of 30.8. This zeolite had been synthesized in accordance with the teaching of EP-B1-0 042 226. To prepare such a zeolite, the reaction mixture had the following molar composition: 60 $SiO_2$: 10.6 $Na_2O$; 5.27 NaBr: 1.5 $Al_2O_3$: 19.5 Hexa-$Br_2$: 2777$H_2O$. Hexa-$Br_2$ was 1,6-N,N,N,N',N',N',-hexamethylhexamethylene diammonium; bromine was the counter-ion. The reaction mixture was placed in a stirred autoclave (300 rpm) for 5 days at 180° C.

This EU-1 zeolite initially underwent dry calcining at 550° C. in a stream of dry air for 24 hours to eliminate the organic template. Next, the solid obtained underwent four ion exchanges in a 10N $NH_4NO_3$ solution at about 100° C. for 4 hours for each exchange. The solid obtained was denoted EU-1 (1) and had an overall Si/Al atomic ratio of 15.3 and a Na/Al atomic ratio of 0.51%.

The EU-1 zeolite then underwent 3 successive acid attacks using 2N, 5N then 8N nitric acid at about 100° C. for 4 hours. The volume V of the nitric acid solution used (in ml) was equal to 10 times the weight P (in grams) of dry EU-1 zeolite (V/P=10). Between each of the acid attacks, the zeolite was washed with water. Next, the zeolite was dried overnight at 120° C.

At the end of these treatments, the EU-1 (2) zeolite was obtained which had an overall Si/Al atomic ratio measured by X ray fluorescence of 21.35 and a Na/Al atomic ratio of less than 0.2%. Thus, 28.3% of the aluminium atoms present in the as-synthesized EU-1 zeolite had been extracted.

Example 2

(Not in Accordance with the Invention): Preparation of Catalyst A Comprising a Non-Dealuminated EU-1 Zeolite The EU-1 zeolite (1) obtained in Example 1 was formed by extrusion with an alumina gel to obtain, after drying at a temperature of 100° C. overnight and calcining in dry air brought to a temperature of 450° C. for 4 hours, the support S1 which contained 15% by weight of EU-1 zeolite and 85% of alumina.

This support S1 underwent anion exchange with hexachloroplatinic acid in the presence of hydrochloric acid as a competing agent, in order to deposit 1% by weight of platinum with respect to the weight of catalyst. The moist solid was then dried at 120° C. for 12 hours and calcined in a flow of dry air at a temperature of 500° C. for one hour.

Catalyst A obtained contained 15% by weight of EU-1 zeolite, 84% by weight of alumina and 1% by weight of platinum.

Example 3

(In Accordance with the Invention): Preparation of Catalyst B Comprising a Dealuminated EU-1 Zeolite The dealuminated EU-1 (2) zeolite obtained in Example 1 was formed by extrusion with an alumina gel to obtain, after drying at a temperature of 100° C. overnight and calcining in dry air brought to a temperature of 450° C. for 4 hours, the support S2 which contained 15% by weight of dealuminated EU-1 zeolite and 85% by weight of alumina.

This support S2 underwent anion exchange with hexachloroplatinic acid in the presence of hydrochloric acid as a competing agent, in order to deposit 1% by weight of platinum with respect to the weight of catalyst. The moist solid was then dried at 120° C. for 12 hours and calcined in a flow of dry air at a temperature of 500° C. for one hour.

Catalyst B obtained contained 15% by weight of dealuminated EU-1 zeolite, 84% by weight of alumina and 1% by weight of platinum.

Example 4

(Not in Accordance with the Invention): Preparation of Catalyst C Comprising a Non-Dealuminated EU-1 Zeolite The starting material used was an as-synthesized EU-1 zeolite comprising the organic template, namely 1,6-N,N,N,N',N',N',-hexamethylhexamethylene diammonium, which had an overall Si/Al atomic ratio of 21.35, and a sodium weight content corresponding to a Na/Al atomic ratio (as a %) of 27.4. This zeolite had been synthesized in accordance with the teaching of EP-B1-0 042 226. To prepare such a zeolite, the reaction mixture had the following molar composition: 60

SiO$_2$: 10.6 Na$_2$O; 5.27 NaBr: 1 Al$_2$O$_3$: 19.5 Hexa-Br$_2$: 2777H$_2$O. Hexa-Br$_2$ was 1,6-N,N,N,N',N',N',-hexamethylhexamethylene diammonium; bromine was the counter-ion. The reaction mixture was placed in a stirred autoclave (300 rpm) for 4 days at 180° C.

This EU-1 zeolite initially underwent dry calcining at 550° C. in a stream of dry air for 24 hours. Next, the solid obtained underwent four ion exchanges in a 10N NH$_4$NO$_3$ solution at about 100° C. for 4 hours for each exchange. The solid obtained was denoted EU-1 (3) and had an overall Si/Al atomic ratio of 21.35 and a Na/Al atomic ratio of 0.52%.

The EU-1 (3) zeolite obtained was then formed by extrusion with an alumina gel to obtain, after drying at a temperature of 100° C. overnight and calcining in dry air at 450° C. for 4 hours, the support S3 which contained 15% by weight of EU-1 zeolite and 85% of alumina.

This support S3 underwent anion exchange with hexachloroplatinic acid in the presence of hydrochloric acid as a competing agent, in order to deposit 1% by weight of platinum with respect to the weight of catalyst. The moist solid was then dried at 120° C. for 12 hours and calcined in a flow of dry air at a temperature of 500° C. for one hour.

Catalyst C obtained contained 15% by weight of EU-1 zeolite, 84% by weight of alumina and 1% by weight of platinum.

Example 5

Evaluation of Catalytic Properties of Catalysts A, B and C for the Isomerization of Ethylbenzene The feed to be isomerized, brought into contact with catalyst A, with catalyst B then with catalyst C, was exclusively constituted by ethylbenzene.

The operating conditions for isomerization were as follows:
 temperature: 410° C.;
 total pressure: 10 bars (1 bar=0.1 MPa);
 partial pressure of hydrogen: 8 bars;
 feed: ethylbenzene;
 space velocity, expressed in kilograms of feed introduced per kilogram of catalyst per hour, of 8.7 h$^{-1}$.

The catalytic properties of catalysts A, B and C were evaluated in succession for the isomerization of ethylbenzene. Each catalyst was reduced in hydrogen for 4 hours at 480° C. before injecting the feed.

The catalysts were evaluated in terms of selectivity. In addition to the desired reaction corresponding to the isomerization of ethylbenzene which produces xylenes, side reactions produced three types of by-products: paraffins essentially resulting from napthene ring opening reactions followed by cracking, aromatics formed by disproportionation and transalkylation of aromatics containing 8 carbon atoms (AC8), and finally naphthenes including naphthenes containing 8 carbon atoms (N8) formed by the hydrogenation of aromatics. The N8s could be recycled and so the selectivities of products other than naphthenes were compared.

The selectivity towards the various products of the isomerization reaction was calculated using the yields of these various products. The yields were determined from the % by weight of the various products obtained by analysis of the effluents and were calculated as follows:

Isomerization yield: Σ xylenes;

Disproportionation yield: 2×106/134×DEB (diethylbenzene);

Dealkylation yield: 106/30×C$_2$ (ethane);

Transalkylation yield: 106/134×DMEB (dimethylethylbenzene)+106/120×ET (ethyltoluene);

Napthenes yield: 106/84×ΣN$_6$ (naphthenes containing 6 carbons)+106/98×ΣN$_7$ (naphthenes containing 7 carbons)+106/112×ΣN$_8$ (naphthenes containing 8 carbons);

Cracking products yield: ΣC$_3$+C$_4$+C$_5$+C$_6$ (C$_3$-C$_6$ aliphatics);

Selectivity for product "i" other than napthenes: (yield of product i)/(Σyield−naphthenes yield).

TABLE 1

Selectivity for reaction products (%) other than naphthenes on catalysts A, B and C after 4000 min of reaction

| Selectivity (%) | Catalyst A | Catalyst B | Catalyst C |
| --- | --- | --- | --- |
| Isomerization | 68.1 | 73.0 | 64.3 |
| Disproportionation | 16.3 | 12.2 | 18.4 |
| Dealkylation | 5.0 | 5.0 | 5.5 |
| Cracking | 9.6 | 7.8 | 10.6 |
| Transalkylation | 1.0 | 1.0 | 1.2 |

The results shown in Table 1 demonstrate that catalyst B comprising a dealuminated EU-1 zeolite wherein at least 10% by weight of the aluminium atoms have been extracted from the as-synthesized EU-1 zeolite performed much better catalytically in terms of selectivity than those obtained using catalysts A and C comprising a non-dealuminated EU-1 zeolite. In particular, the use of catalyst B to isomerize ethylbenzene resulted in a substantial improvement in the isomerization selectivity to the detriment of the selectivity for disproportionation, dialkylation, transalkylation and cracking.

The preceding examples can be repeated with similar success by substituting the generically or specifically described reactants and/or operating conditions of this invention for those used in the preceding examples.

The entire disclosures of all applications, patents and publications, cited herein and of corresponding French application Ser. No. 07/02.941, filed Apr. 23, 2007, are incorporated by reference herein.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A process for isomerising an aromatic cut containing at least one aromatic compound containing eight carbon atoms per molecule, comprising bringing said cut into contact with at least one catalyst containing at least one zeolite with structure type EUO, said catalyst having been prepared using a process comprising at least the following steps:
  i) synthesizing at least one zeolite with structure type EUO having an overall Si/Al atomic ratio in the range 5 to 45;
  ii) dealuminating the zeolite obtained at the end of said step i) using at least one treatment with an aqueous solution of a mineral acid or an organic acid, such that at least 10% by weight of the aluminium atoms are extracted from said zeolite resulting from said step i);
  iii) forming said dealuminated zeolite with a matrix;
  iv) depositing at least one metal from group VIII of the periodic table of the elements, the order of carrying out said steps iii) and iv) being optional following on from said step ii).

2. An isomerization process according to claim 1, in which said zeolite with structure type EUO present in said catalyst is an EU-1 zeolite.

3. An isomerization process according to claim 1, in which said zeolite with structure type EUO obtained at the end of said step i) has an overall Si/Al atomic ratio in the range 10 to 25.

4. An isomerization process according to claim 1, in which said step ii) comprises extracting at least 20% by weight of aluminium atoms from said zeolite with structure type EUO resulting from said step i).

5. An isomerization process according to claim 1, in which in order to carry out said step ii), the zeolite with structure type EUO resulting from said step i) undergoes calcining in a stream of dry air at a temperature in the range 400° C. to 600° C. then undergoes at least one treatment with an aqueous solution of a mineral acid or an organic acid.

6. An isomerization process according to claim 5, further comprising conducting one or more ion exchange step(s) with at least one $NH_4NO_3$ solution is (are) between the calcining in a stream of dry air and the treatment using said aqueous acid solution.

7. An isomerization process according to claim 5, in which treatment of the zeolite with an aqueous solution of a mineral acid or an organic acid is carried out at a temperature in the range 30° C. to 120° C., the concentration of the acid in said aqueous solution being in the range 0.05 to 20 mol/l, the ratio between the volume of the acid solution in ml and the weight of the zeolite treated in grams being in the range 1 to 50, the duration of the acid treatment being more than 1 hour.

8. An isomerization process according to claim 1, in which said acid is a nitric acid, hydrochloric acid or sulphuric acid.

9. An isomerization process according to claim 5, comprising less than 4 successive treatments of the zeolite with an aqueous acidic solution.

10. An isomerization process according to claim 1, in which in order to carry out said step ii), the zeolite with structure type EUO resulting from said step i) undergoes calcining in a stream of dry air at a temperature in the range 400° C. to 600° C. then undergoes one or more ion exchange (s) using at least one $NH_4NO_3$ solution, then undergoes at least one cycle for dealumination of the zeolitic framework comprising at least one heat treatment carried out in the presence of steam and at least one acid attack using at least one aqueous solution of a mineral or organic acid.

11. An isomerization process according to claim 1, in which, in order to carry out said step ii), the zeolite with structure type EUO resulting from said step i) undergoes heat treatment carried out in the presence of steam at a temperature in the range 450° C. to 850° C. then undergoes at least one treatment with an aqueous solution of a mineral or organic acid.

12. An isomerization process according to claim 1, in which said step iii) precedes said step iv).

13. An isomerization process according to claim 1, in which said matrix used in step iii) is an alumina.

14. An isomerization process according to claim 1, in which said group VIII metal used to carry out said step iv) is platinum.

15. An isomerization process according to claim 1, further comprising introducing at least one metal selected from metals from groups IIIA, IVA and VIIB is introduced to carry out said step iv).

16. An isomerization process according to claim 1, carried out under the following operating conditions: a temperature in the range 300° C. to 500° C., a partial pressure of hydrogen in the range 0.3 to 1.5 MPa, a total pressure in the range 0.45 to 1.9 MPa and a space velocity, expressed in kilograms of feed introduced per kilogram of catalyst per hour, in the range 0.25 to 30 $h^{-1}$.

* * * * *